United States Patent
Kurz et al.

(10) Patent No.: US 6,951,725 B2
(45) Date of Patent: Oct. 4, 2005

(54) IN VITRO PROTEIN INTERACTION DETECTION SYSTEMS

(75) Inventors: Markus Kurz, Newton, MA (US); Peter Lohse, Weston, MA (US)

(73) Assignee: Compound Therapeutics, Inc., Waltham, MA (US)

(*) Notice: Subject to any disclaimer, the term of this patent is extended or adjusted under 35 U.S.C. 154(b) by 482 days.

(21) Appl. No.: 10/176,826

(22) Filed: Jun. 20, 2002

(65) Prior Publication Data

US 2003/0013110 A1 Jan. 16, 2003

Related U.S. Application Data

(60) Provisional application No. 60/300,267, filed on Jun. 21, 2001.

(51) Int. Cl.[7] ................................................. C12Q 1/68
(52) U.S. Cl. ........................................................ 435/6
(58) Field of Search .............................................. 435/6

(56) References Cited

U.S. PATENT DOCUMENTS 6,416,950 B1 * 7/2002 Lohse et al. ................... 435/6

* cited by examiner

*Primary Examiner*—Terry McKelvey
(74) *Attorney, Agent, or Firm*—Fish & Neave IP Group Ropes & Gray, LLP (57) ABSTRACT

Disclosed herein are in vitro assays for the identification of interactions between proteins or other molecules, the identification of transcriptional activator proteins, and the detection of compounds that inhibit protein/protein or protein/compound interactions. Also disclosed herein are in vitro assays for the selection of interacting proteins and transcriptional activator proteins out of libraries.

7 Claims, 9 Drawing Sheets

Two-Hybrid Systems

Three-Hybrid Systems

One-Hybrid System

Fig. 3

Reverse Two-Hybrid System

Fig. 4

Construction of DNA-Peptide Fusions for In Vitro n-Hybrid Systems - I

Fig. 5

Construction of DNA-Peptide Fusions for *In Vitro* n-Hybrid Systems - II

Fig. 6

Construction of DNA-Peptide Fusions for *In Vitro* n-Hybrid Systems - III

Fig. 7

Construction of DNA-Peptide Fusions for *In Vitro* n-Hybrid Systems – IV

Fig. 8

Two-Hybrid *In Vitro* Selection

Fig. 9

IN VITRO PROTEIN INTERACTION DETECTION SYSTEMS

CROSS REFERENCE TO RELATED APPLICATIONS

This application claims the benefit of the U.S. provisional application, U.S. Ser. No. 60/300,267, filed Jun. 21, 2001.

BACKGROUND OF THE INVENTION

In general, the invention relates to in vitro techniques for detecting interactions of proteins with other proteins or compounds, and for selecting such interacting proteins.

In eukaryotic cells, the expression of individual genes is tightly regulated on the level of mRNA transcription. The cellular transcription machinery consists of a multi-component complex that includes RNA polymerase II and several associated proteins (Tjian & Maniatis, Cell (1994) vol. 77, p. 5–8). Transcription is initiated by binding of the polymerase complex to a core promoter sequence located upstream of the corresponding gene. This binding process is greatly facilitated by transcription activators that bind to DNA sites outside the core promoter and recruit the polymerase complex through additional non-covalent interactions (Ptashne & Gann, Nature (1997) vol. 386, p. 569–77).

Figure 1:
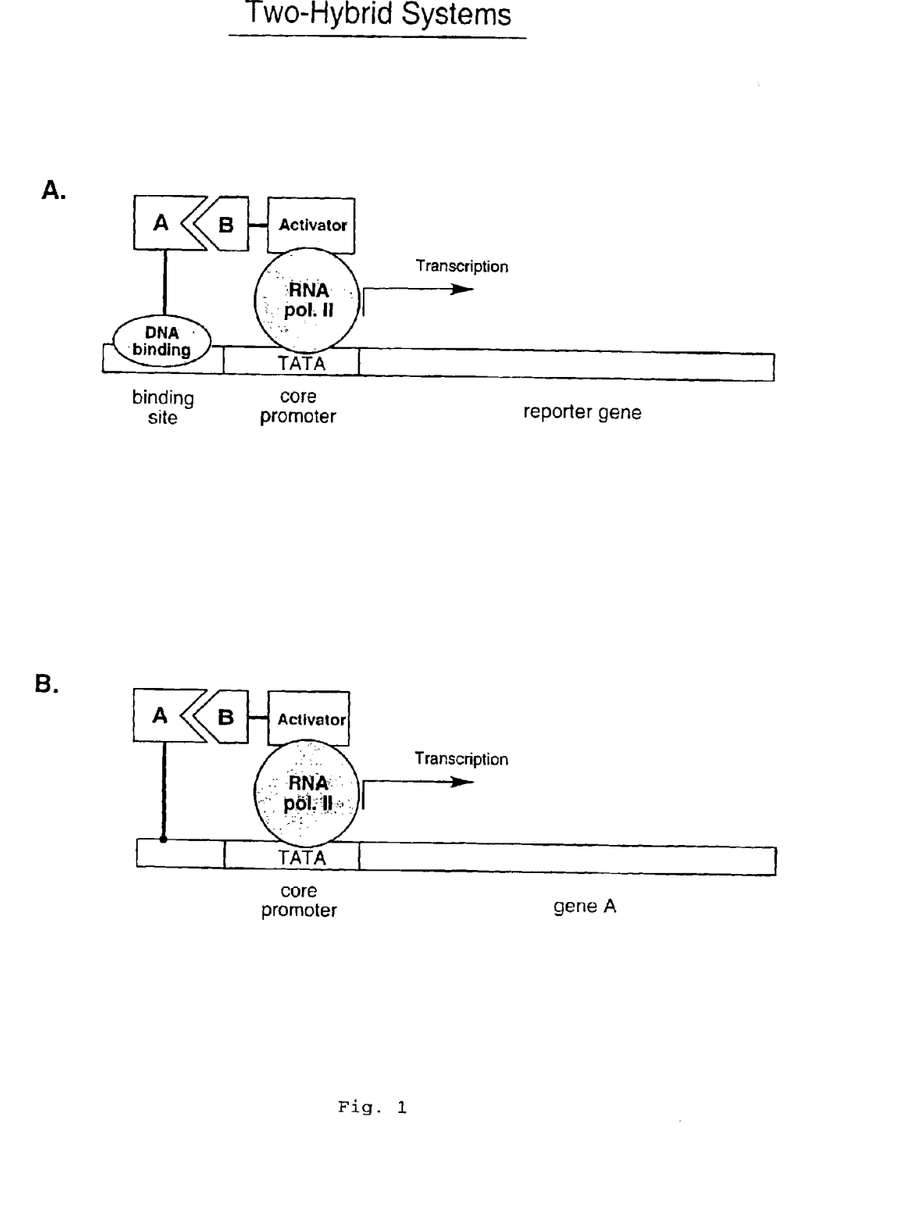
FIG. 1A is a schematic drawing illustrating a conventional two-hybrid system. In this system, binding interactions between "A" and "B" allow recruitment of RNA polymerase II through an activator domain, resulting in the triggering of reporter gene transcription. "A" associates with the gene by non-covalent binding. In this system, there is no correlation between the reporter gene sequence and any of the protein components utilized.
FIG. 1B is a schematic drawing illustrating an in vitro two-hybrid system using DNA-protein fusions. In this system, the protein portion "A" is covalently attached to its encoding gene. Binding to "B" triggers the recruitment of the polymerase complex and leads to the transcription of RNA that carries the genetic information for "A."
Figure 2:
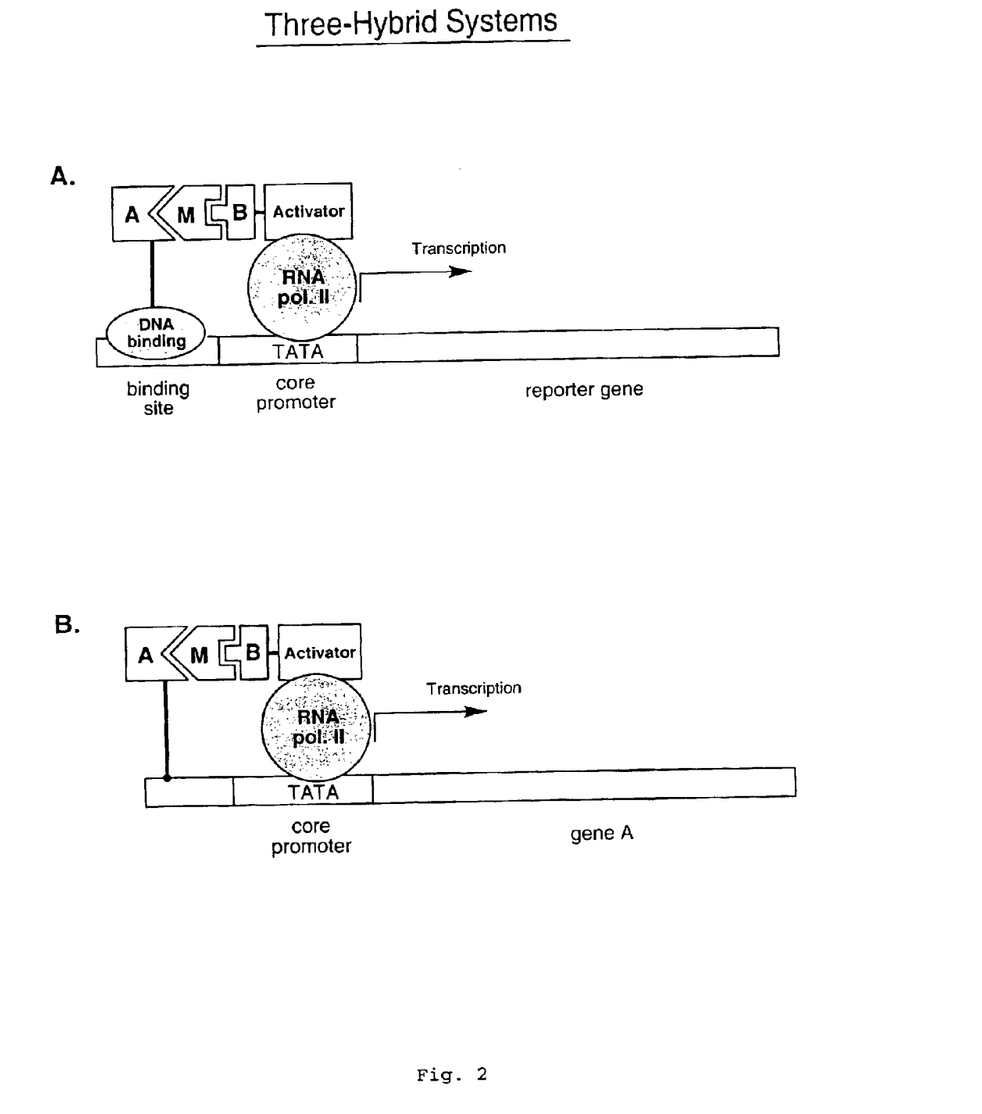
FIG. 2A is a schematic drawing illustrating a conventional three-hybrid system. This system is similar to the conventional two-hybrid system of FIG. 1A, except that there is no direct interaction between "A" and "B." These components instead interact through a third component, the adaptor or mediator "M."
FIG. 2B is a schematic drawing illustrating an in vitro three-hybrid system using DNA-protein fusions. In this system, the mediator "M" facilitates the formation of a complex that triggers transcription of gene A.

In order to be effective, the linkage between the DNA-binding and activation domains of transcription activation factors need not be covalent; indeed, these domains function even when present on separate (but associated) molecular entities. Proximity between the DNA-binding and activator portion of a transcription factor can be restored by either direct dimerization of the components ("A" and "B" in FIG. 1) or through the action of adaptor or mediator molecules ("M" in FIG. 2). Successful gene expression is dependent on the corresponding association event and can serve as a means to test for molecular interactions between those domains. Even relatively weak molecular interactions and those with fast off-rates can trigger transcription over time and can therefore be detected.

Based on this, a number of "two-hybrid" (FIG. 1A; Fields & Song, Nature (1989) vol. 340, p. 245–246) and "three-hybrid" systems (FIG. 2A; Sengupta et al., Proc. Natl. Acad. Sci. USA (1996) vol. 93, p. 8496–8501; Lictria & Liu, Proc. Natl. Acad. Sci. USA (1996) vol. 93, p. 12817) have been devised for the identification of protein/protein and drug/protein interactions (for reviews see e.g.: Kolanus, Curr Top Microbiol Immunol. (1999) vol. 243, p. 37–54; Vidal & Legrain, Nucleic Acids Res. (1999) vol. 27, p. 4; Drees, Curr. Opinion Chem. Biol. (1999) vol. 3, p. 64–70). These assays, however, are somewhat restricted when applied to the screening of peptide or protein libraries. Since genotype (i.e, the plasmid encoding an individual library member) and phenotype (i.e., the protein library member itself) are not covalently linked, their association must be maintained within the confines of a cell. Accordingly, these assays must be performed in in vivo expression systems, generally, in yeast cells. This imposes several limitations resulting, for example, from the restriction of effective library size by transformation efficiencies, the occurrence of unwanted selection pressure inside a cellular environment, the need to exclude molecules that exhibit toxic effects on cells, and the difficulty in delivering certain drugs to the cytoplasm of cells (see, for example, Roberts, Curr. Opin. Biotech. (1999) vol. 3, p. 268–273). Accordingly, new approaches to the detection of protein/protein and protein/compound interactions are desirable.

SUMMARY OF THE INVENTION

The present invention provides such novel approaches to the detection of protein/protein and protein/compound interactions. In particular, in a first aspect, the invention features a method for determining whether a protein interacts with a target compound in vitro, the method involving the steps of: (a) providing a DNA-protein fusion molecule, (i) a double-stranded DNA having a core promoter operably linked to a nucleic acid sequence, and (ii) a protein covalently attached to the DNA; (b) providing a target compound fusion molecule including a target compound covalently attached to a transcription activation domain; (c) contacting the DNA-protein fusion molecule with the target compound fusion molecule in an in vitro transcription system under conditions that allow the target compound fusion molecule to interact with the protein of the DNA-protein fusion molecule, wherein an interaction recruits RNA polymerase and triggers transcription of said nucleic acid sequence; and (d) detecting increased transcription of the nucleic acid sequence, or a portion thereof, in the presence of said target compound fusion molecule as an indication that the protein of the DNA-protein fusion interacts with the target compound of the target compound fusion molecule.

In a related aspect, the invention also features a method for determining whether a protein interacts in vitro with a target compound through an adaptor molecule, the method involving the steps of: (a) providing a DNA-protein fusion molecule including (i) a double-stranded DNA having a core promoter operably linked to a nucleic acid sequence, and (ii) a protein covalently attached to the DNA; (b) providing a target compound fusion molecule including a target compound covalently attached to a transcription activation domain; (c) contacting the DNA-protein fusion molecule with the target compound fusion molecule in the presence of an adaptor molecule, wherein the adaptor molecule is necessary for an interaction to occur between the protein of the DNA-protein fusion molecule and the target compound fusion molecule, the contacting being carried out in an in vitro transcription system under conditions that allow the DNA-protein fusion molecule, the adaptor molecule, and the target compound fusion molecule to interact, wherein an interaction recruits RNA polymerase and triggers transcription of the nucleic acid sequence; and (d) detecting increased transcription of the nucleic acid sequence, or a portion thereof, in the presence of the target compound fusion molecule as an indication that the protein of the DNA-protein fusion interacts with the target compound of the target compound fusion molecule in the presence of the adaptor molecule.

In a second aspect, the invention features a method of identifying a transcriptional activator protein in vitro, the method involving the steps of: (a) providing a DNA-protein fusion molecule including (i) a double-stranded DNA having a core promoter operably linked to a nucleic acid sequence, and (ii) a protein covalently attached to the DNA; (b) adding the DNA-protein fusion molecule to an in vitro transcription system under conditions wherein a transcriptional activator protein recruits RNA polymerase and triggers transcription of the nucleic acid sequence; and (c) detecting whether there is an occurrence of increased transcription of the nucleic acid sequence, or a portion thereof, in the presence of the DNA-protein fusion molecule, wherein increased transcription indicates that the protein portion of the DNA-protein fusion molecule is a transcriptional activator protein.

In a third aspect, the invention features a method of detecting a compound that inhibits the in vitro interaction between a protein and a target compound, the method involving the steps of: (a) providing a DNA-protein fusion molecule including (i) a double-stranded DNA having a core promoter operably linked to a nucleic acid sequence, and (ii)

a protein covalently attached to the DNA; (b) providing a target compound fusion molecule including a target compound covalently attached to a transcription activation domain, wherein the target compound of the target compound fusion molecule interacts with the protein of the DNA-protein fusion molecule, resulting in recruitment of RNA polymerase and transcription of the nucleic acid sequence; (c) contacting the DNA-protein fusion molecule with the target compound fusion molecule in the presence of a candidate inhibitor molecule, the contacting being carried out in an in vitro transcription system under conditions that allow the protein of the DNA-protein fusion molecule, the target compound fusion molecule, and the candidate inhibitor molecule to interact, wherein an interaction of the inhibitor molecule with the protein of the DNA-protein fusion molecule and/or the target compound fusion molecule inhibits recruitment of RNA polymerase and inhibits transcription of the nucleic acid sequence; and (d) detecting decreased transcription of the nucleic acid sequence, or a portion thereof, in the presence of the candidate inhibitor molecule as an indication that the candidate inhibitor molecule inhibits an interaction between the protein of the DNA-protein fusion molecule and the target compound of the target compound fusion molecule.

In a related aspect, the invention also features a method of detecting a compound that inhibits the in vitro interaction between a protein, a target compound, and an adaptor molecule, the method involving the steps of: (a) providing a DNA-protein fusion molecule including (i) a double-stranded DNA having a core promoter operably linked to a nucleic acid sequence, and (ii) a protein covalently attached to the DNA; (b) providing a target compound fusion molecule including a target compound covalently attached to a transcription activation domain, wherein the target compound of the target compound fusion molecule interacts with the protein of the DNA-protein fusion molecule in the presence of an adaptor molecule, resulting in recruitment of RNA polymerase and transcription of the nucleic acid sequence; (c) contacting the DNA-protein fusion molecule with the target compound fusion molecule and the adaptor molecule in the presence of a candidate inhibitor molecule, the contacting being carried out in an in vitro transcription system under conditions that allow the DNA-protein fusion molecule, the target compound fusion molecule, the adaptor molecule, and the candidate inhibitor molecule to interact, wherein an interaction of said inhibitor molecule with the protein of the DNA-protein fusion molecule, the adaptor molecule, and/or the target compound fusion molecule inhibits recruitment of RNA polymerase and inhibits transcription of the nucleic acid sequence; and (d) detecting decreased transcription of the nucleic acid sequence, or a portion thereof, in the presence of the candidate inhibitor molecule as an indication that the candidate inhibitor molecule inhibits an interaction between either the protein of the DNA-protein fusion molecule and the adaptor molecule or the target compound of the target compound fusion molecule and the adaptor molecule.

In yet another related aspect, the invention features a method of detecting a compound that in vitro inhibits a transcriptional activator protein, the method comprising the steps of: (a) providing a DNA-protein fusion molecule including (i) a double-stranded DNA having a core promoter operably linked to a nucleic acid sequence, and (ii) a protein covalently attached to the DNA; (b) contacting the DNA-protein fusion molecule with a candidate inhibitor molecule, the contacting being carried out in an in vitro transcription system under conditions that allow the DNA-protein fusion molecule and the candidate inhibitor molecule to interact; and (c) detecting decreased transcription of the nucleic acid sequence, or a portion thereof, in the presence of the candidate inhibitor molecule as an indication that the candidate inhibitor molecule inhibits the transcriptional activator protein.

In a fourth aspect, the invention further features a method of selecting for a nucleic acid sequence encoding a protein that interacts with a target compound in vitro, the method involving the steps of: (a) providing a population of DNA-protein fusion molecules, each of the fusion molecules including (i) a double-stranded DNA having a core promoter operably linked to a nucleic acid sequence, the nucleic acid sequence including an open reading frame positioned in antisense orientation relative to the core promoter, and (ii) a protein covalently attached to the DNA, the protein being encoded by the open reading frame; (b) providing a target compound fusion molecule including a target compound covalently attached to a transcription activation domain; (c) contacting the population of DNA-protein fusion molecules with the target compound fusion molecule in an in vitro transcription system under conditions that allow the target compound fusion molecule to interact with the DNA-protein fusion molecules, wherein an interaction between the target compound fusion molecule and one or more DNA-protein fusion molecules recruits RNA polymerase and triggers transcription to produce one or more initial RNA transcripts of the nucleic acid sequence; (d) isolating the one or more initial RNA transcripts of the nucleic acid sequences produced in step (c); (e) generating one or more double-stranded DNA molecules from the one or more initial RNA transcripts of step (d); (f) transcribing the one or more double-stranded DNA molecules of step (e) to produce one or more secondary RNA transcripts; (g) generating one or more DNA-protein fusion molecules from the one or more secondary RNA transcripts of step (f); and (h) repeating steps (b)–(d), and optionally step (e), using the one or more DNA-protein fusion molecules formed in step (g), thereby selecting for a nucleic acid sequence encoding a protein that interacts with a target compound.

In a related aspect, the invention also features a method of selecting for a nucleic acid sequence encoding a protein that interacts in vitro with a target compound through an adaptor molecule, the method involving the steps of: (a) providing a population of DNA-protein fusion molecules, each of the fusion molecules including (i) a double-stranded DNA having a core promoter operably linked to a nucleic acid sequence, the nucleic acid sequence including an open reading frame positioned in antisense orientation relative to the core promoter, and (ii) a protein covalently attached to the DNA, the protein being encoded by the open reading frame; (b) providing a target compound fusion molecule including a target compound covalently attached to a transcription activation domain; (c) contacting the population of DNA-protein fusion molecules with the target compound fusion molecule in the presence of an adaptor molecule, wherein the adaptor molecule is necessary for an interaction to occur between the DNA-protein fusion molecules and the target compound fusion molecule, the contacting being carried out in an in vitro transcription system under conditions that allow one or more of the DNA-protein fusion molecules, the adaptor molecule, and the target compound fusion molecule to interact, wherein an interaction recruits RNA polymerase and triggers transcription to produce one or more initial RNA transcripts of the nucleic acid sequence; (d) isolating the one or more initial RNA transcripts of the nucleic acid sequence produced in step (c); (e) generating one or more double-stranded DNA molecules from the one or more initial RNA transcripts of step (d); (f) transcribing the one or more double-stranded DNA molecules of step (e) to produce one or more secondary RNA transcripts; (g) generating one or more DNA-protein fusion molecules from the one or more secondary RNA transcripts of step (f); and (h) repeating steps (b)–(d), and optionally step (e), using the one or more DNA-protein fusion molecules formed in step (g), thereby selecting for a nucleic acid sequence encoding a protein that interacts with a target compound through an adaptor molecule.

In yet another related aspect, the invention features a method of selecting in vitro for a nucleic acid encoding a transcriptional activator protein, the method involving the steps of (a) providing a population of candidate DNA-protein fusion molecules, each of the fusion molecules including (i) a double-stranded DNA having a core promoter operably linked to a nucleic acid sequence, the nucleic acid sequence including an open reading frame positioned in antisense orientation relative to the core promoter, and (ii) a protein covalently attached to the DNA, the protein being encoded by the open reading frame; (b) adding the population of candidate DNA-protein fusion molecules to an in vitro transcription system, wherein a transcriptional activator protein triggers transcription to produce an initial RNA transcript of the nucleic acid sequence; (c) isolating the one or more initial RNA transcripts of the nucleic acid sequence produced in step (b); (d) generating one or more double-stranded DNA molecules from the one or more initial RNA transcripts of step (c); (e) transcribing the one or more double-stranded DNA molecules of step (d) to produce one or more secondary RNA transcripts; (f) generating (for example, by RT-PCR) one or more DNA-protein fusion molecules from the one or more secondary RNA transcripts of step (e); and (g) repeating steps (b)-(c), and optionally step (d), using the one or more DNA-protein fusion molecules formed in step (f), thereby selecting for a nucleic acid sequence encoding a transcriptional activator protein.

In preferred embodiments of any of the above aspects of the invention, the target compound is a protein, a nucleic acid, or a small molecule. In other preferred embodiments, the in vitro transcription system includes a nuclear extract; the transcription activation domain is the herpesvirus VP16 polypeptide; and/or the DNA-protein fusion is characterized by the protein being covalently attached to the DNA 5' to the core promoter.

In these methods, the target compound fusion molecule is preferably produced by expression of a nucleic acid encoding the target compound fusion molecule or by chemical coupling of the target compound and the transcription activation domain.

In a final aspect, the invention features a DNA-protein fusion molecule that includes: (a) a double-stranded DNA having a core promoter operably linked to a nucleic acid sequence; and (b) a protein covalently attached to the DNA. In this fusion molecule, the protein is preferably covalently attached to the DNA upstream of the core promoter, and the nucleic acid sequence preferably includes an open reading frame that encodes the protein positioned in antisense orientation relative to the core promoter. Such a fusion molecule may be generated using a bulged linker molecule.

As used herein, by a "protein" is meant any two or more naturally occurring or modified amino acids joined by one or more peptide bonds. "Protein," "peptide," and "polypeptide" are used interchangeably herein.

By a "nucleic acid" is meant any two or more covalently bonded nucleotides or nucleotide analogs or derivatives. As used herein, this term includes, without limitation, DNA, RNA, and PNA. By "DNA" is meant a sequence of two or more covalently bonded, naturally occurring or modified deoxyribonucleotides.

By a "target compound" is meant any molecule of interest including, without limitation, any protein, nucleic acid, small molecule, or portion or analog thereof. Proteins (for example, therapeutic proteins or biologically important proteins) represent preferred targets, as do therapeutic drugs, such as small molecule drugs.

By an "open reading frame" is meant any contiguous sequence of two or more codons. Open reading frames according to the invention may encode naturally-occurring proteins or fragments or variants thereof, or may encode synthetic proteins having little or no homology to any known natural sequence.

By a "core promoter" is meant a nucleic acid sequence that is sufficient for the binding of RNA polymerase and initiation of basal transcription.

By a "transcription activation domain" is meant any protein moiety that can promote transcription from an operably associated promoter. Such a domain may be obtained from a naturally-occurring transcriptional activator, or fragment or variant thereof, or may be a synthetic domain. Similarly, a "transcriptional activator protein" is a protein that can promote transcription from an operably associated promoter and that may be a naturally-occurring protein, or a fragment or variant thereof, or a protein that is all or partially synthetic in sequence. A "transcription activation domain" or "transcriptional activator protein" according to the invention preferably increases the transcription from an operably associated promoter by at least 10-fold, more preferably, at least 100-fold, and, most preferably, 1000-fold, relative to basal transcription in the absence of the transcription activation domain or transcriptional activator protein.

By "in vitro transcription system" is meant any reaction mixture that includes RNA polymerase II and facilitates the initiation, synthesis, and completion of RNA transcripts in the presence of a DNA sequence having a functional transcription initiation site and a transcriptional activator protein (or other protein having a transcription activation domain).

By an "adaptor molecule" is meant any molecule that facilitates an interaction between two other molecules, in this case, a protein and target molecule. Adaptor molecules include, without limitation, proteins, nucleic acids, and organic compounds.

By "inhibits the interaction" is meant specifically interferes with or otherwise decreases an interaction, in this case, between a protein and a target compound. In the methods described herein, such inhibition is measured by a decrease in a transcription product, the presence of which is dependent upon the interaction of these components. Inhibitors according to the invention do not include general inhibitors of transcription, for example, compounds that generally block the transcription machinery, change the pH or buffer conditions of a transcription reaction mixture, or generally deactivate transcription activation domains. Specific inhibitors may be readily identified because they reduce transcription that is mediated by the interacting protein and target compound, but have no significant effect on transcription from other promoters (for example, unrelated control promoters) under identical transcription reaction conditions. Preferably, inhibitors according to the invention mediate at least a 10-fold, more preferably, at least a 100-fold, and, most preferably, at least a 1000-fold, reduction in the transcription triggered by a protein-target compound interaction.

By a "population" is meant two or more molecules. Because the methods of the invention facilitate selections that begin, if desired, with large numbers of candidate molecules, a "population" according to the invention preferably means between $10^5$ and $10^9$ molecules, more preferably, between $10^9$ and $10^{13}$, and, most preferably, between $10^{13}$ and $10^{15}$ molecules By "selecting" is meant substantially enriching for a molecule in a population. As used herein, a "selecting" step provides at least a 2-fold, preferably, a 30-fold, more preferably, a 100-fold, and, most preferably, a 1000-fold enrichment of a desired molecule relative to undesired molecules in a population following the selection step. A selection step may be repeated any number of times, and different types of selection steps may be combined in a given selection scheme.

DETAILED DESCRIPTION

Figure 9:
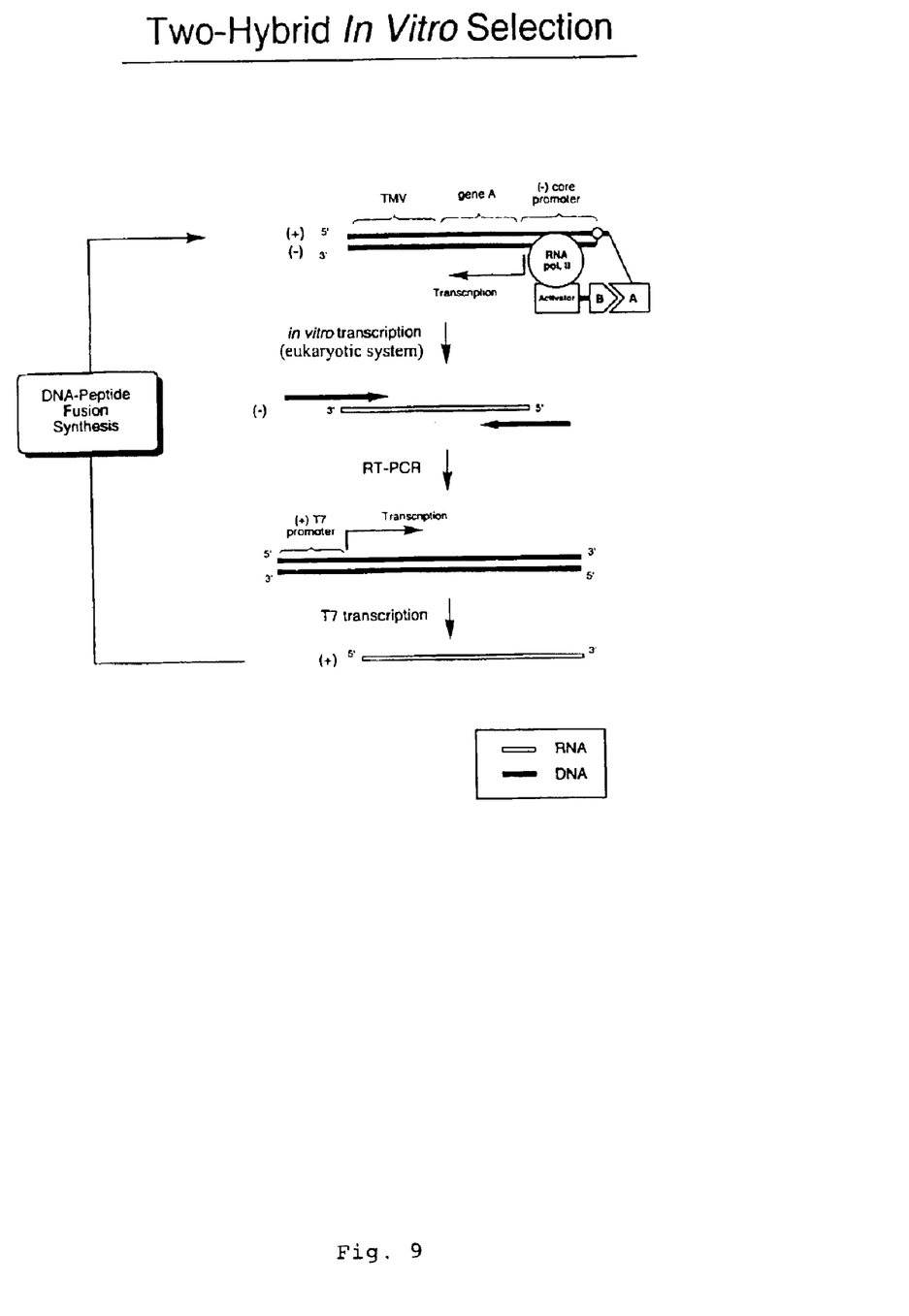
FIG. 9 is a schematic drawing illustrating an exemplary in vitro two-hybrid selection scheme.

Described herein are strategies to perform two-hybrid and three-hybrid experiments entirely in vitro. These assays facilitate the identification of interactions between proteins or other molecules, the identification of transcriptional activator proteins, and the detection of compounds that inhibit protein/protein or protein/compound interactions. In addition, these assays allow for the selection of peptides and proteins with desired properties out of large libraries. To carry out these methods, individual DNA-protein fusions or libraries of such fusions are constructed (for example, as generally described in Lohse et al., WO 00/32823, and in Kurz et al., Chembiochem. (2001) vol. 2, pp. 101–107)). These fusion libraries can include large sets of chimeric molecules in which each protein is covalently bound to its own encoding gene sequence. Binding of a DNA-protein fusion to a suitable target molecule (that is itself covalently attached to a transcription activation domain) results in the recruitment of the transcriptional machinery, and the production of a transcript corresponding to the nucleic acid portion of the DNA-protein fusion molecule (FIG. 1B and FIG. 9). As a result, the genetic information of those proteins that possess appropriate binding affinities for target molecules are expressed as RNA, this RNA being amenable to recovery and amplification for analysis or propagation. Because the expression level of this RNA product is a function of both the strength of the binding interaction and the reaction time, even weak binding interactions can trigger production of significant amounts of RNA if reaction times are sufficient. This provides a distinct advantage over previous affinity-based selection methods in which weak binders are sometimes not well retained on affinity matrices and may be lost during washing steps.

The in vitro nature of the present methods also allows for any number of different types of target molecules to be exploited. These molecules may be fused to activators by recombinant fusion gene production, as in classical in vivo approaches, or importantly may be attached by chemical coupling. This feature of the invention significantly expands the possibilities for target molecules beyond proteins. Preferred target molecules according to the invention include, without limitation, peptides, proteins, and nucleic acids, as well as small molecule drugs.

Figure 3:
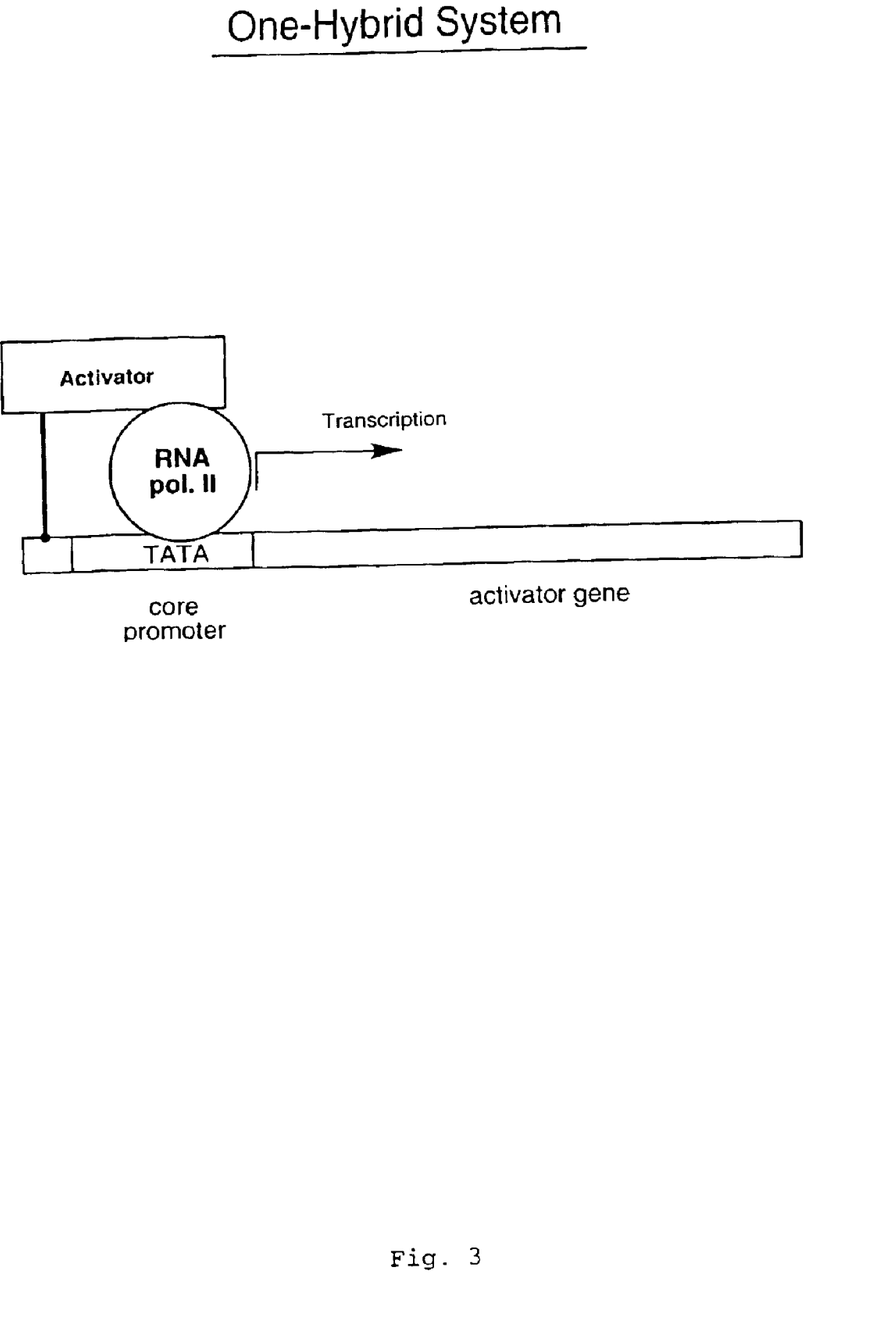
FIG. 3 is a schematic drawing illustrating an in vitro system for detecting transcriptional activator proteins. In this system, a construct that encodes an activator domain promotes transcription of its own activator gene through recruitment of RNA polymerase II.

Transcriptional activators can also be identified by the assays of the present invention. In this embodiment, the protein portion of a DNA fusion itself promotes synthesis of its corresponding RNA, and this transcription product is detected as an indication of a transcriptional activator coding sequence (FIG. 3). This system facilitates a determination of whether a particular protein is capable of transcriptional activation and also enables the in vitro selection of new transcriptional activator proteins, for example, from libraries of candidate fusion molecules.

Apart from applications for selection of peptides, the in vitro two-hybrid (FIG. 1B) and three-hybrid systems (FIG. 2B) described herein also provide the means for the development of diagnostic assays for molecular interactions. In addition, in vitro "reverse two-hybrid" (FIG. 4) and "reverse three-hybrid" systems described herein facilitate the screening of drugs or other compounds that disrupt known molecular interactions.

All procedures described herein in connection with this invention can be performed as true in vitro processes and are therefore free of the limitations usually imposed on in vivo selection methods. Library sizes are not limited by transformation efficiencies and may be significantly higher than in traditional two-hybrid or three-hybrid systems. Moreover, problems that arise from host cell toxicity of certain compounds and drug delivery into cells are avoided. Even proteins that are difficult to express inside cellular environments (for example, extracellular receptors and membrane proteins) can be exploited as targets or diagnostic tools in the present methods. Finally, because the molecular complexity of in vitro transcription systems is generally lower than that of live cells, false positives are also less likely to occur.

The methods of the present invention are now described in detail, including exemplary approaches to the construction of useful DNA-protein fusions. These examples are provided to illustrate the invention, and should not be construed as limiting.

Construction of DNA-Protein Fusion Molecules

The DNA-protein fusions used in the present two-hybrid and three-hybrid experiments preferably include the following key features: (i) an open reading frame encoding the protein of interest (or protein library member) contained within a double stranded DNA; and (ii) a core promoter sequence for basal transcription (Corden et al., Science (1980) vol. 209, p. 1406–1414) located downstream in reverse orientation, i.e. 5'–3' on the antisense strand, followed by the covalently attached protein portion. The construction of such DNA-protein fusions may be performed generally as previously described (Lohse et al., WO 00/32823; Kurz et al., Chembiochem. (2001) vol. 2, pp. 101–107).

Figure 5:
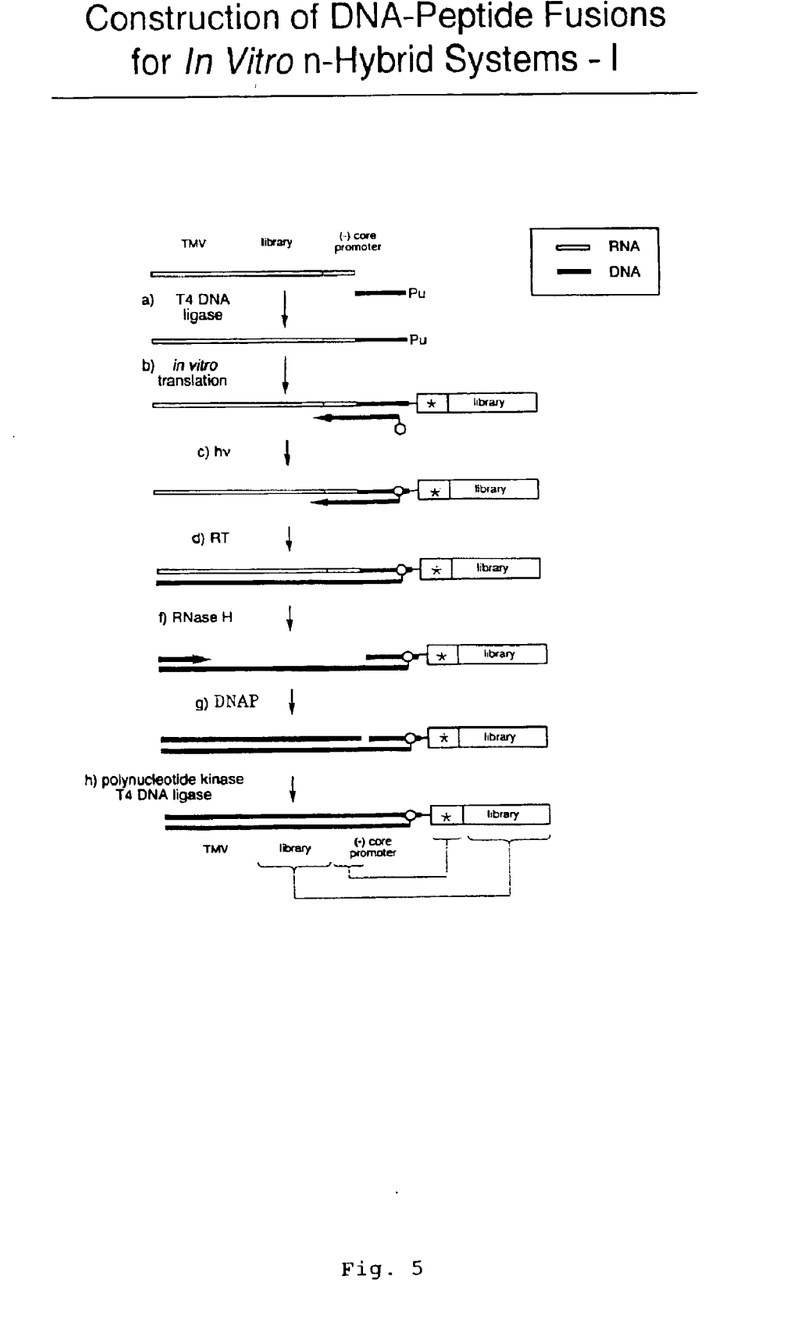
FIG. 5 is a schematic drawing illustrating an exemplary method for the construction of DNA-protein fusions. In this method, combined sequence regions on the RNA and the oligonucleotide linker bearing puromycin serve to generate the core promoter. The portion of the promoter sequence present on the RNA is translated and results in an extension of the protein C-terminus (indicated by an asterisk).

In one preferred approach, illustrated in FIG. 5, a template mRNA is prepared that contains an enhancer region for translation (for example, the 5' untranslated region of tobacco mosaic virus, TMV (Gallie et al., Nucleic Acids Res. (1988) vol. 16, p. 883–893)), followed by an open reading frame that encodes the protein (or protein library member) of interest. The 3'-end of the mRNA may carry a sequence that includes either a portion or the entire (−) core promoter sequence. A DNA-linker that bears a peptide acceptor, such as puromycin, on its 3'-end is attached to the 3'-terminus of the RNA, for example, by enzymatic ligation (Roberts & Szostak, Proc. Natl. Acad. Sci. USA (1997) vol. 94, p. 12297–12302). This linker is preferably about 25 to 30 nucleotides in length (Liu et al., Methods Enzymol. (2000), 318:268). If only a portion of the (−) core promoter is included in the mRNA, the remaining (−) core sequence is provided by all or part of the linker (see FIG. 5). The distribution of the (−) core promoter sequence between the mRNA and DNA linker depends, for example, on the promoter length and its preferred spatial orientation with respect to the peptide attachment point in the final product. In certain instances, it may be desirable to include as much of the promoter sequence as possible in the DNA linker, since the sequence that is contained in the mRNA will be subject to translation and the protein's C-terminal portion therefore cannot be freely chosen.

The RNA-linker construct is used for in vitro translation, for example, as previously described (Roberts & Szostak, Proc. Natl. Acad. Sci. USA (1997) vol. 94, p. 12297–12302; Szostak et al., U.S. Pat. No. 6,258,558 B1; U.S. Pat. No. 6,261,804 B1; Szostak et al., WO 98/31700; WO 00/47775), and RNA-protein fusions are obtained. To these fusions, a reverse transcription primer is attached by psoralen photocrosslinking (hν). Its extension by treatment with reverse transcriptase yields the corresponding cDNA, which can be transformed into dsDNA by RNase digestion followed by second strand synthesis using a suitable forward primer (FIG. 5; Type C2 in Lohse et al., WO 00/32823). The gap between the newly synthesized forward strand and the remaining DNA-linker portion may then be sealed through a kination-ligation procedure, yielding the desired DNA-protein fusions.

Figure 6:
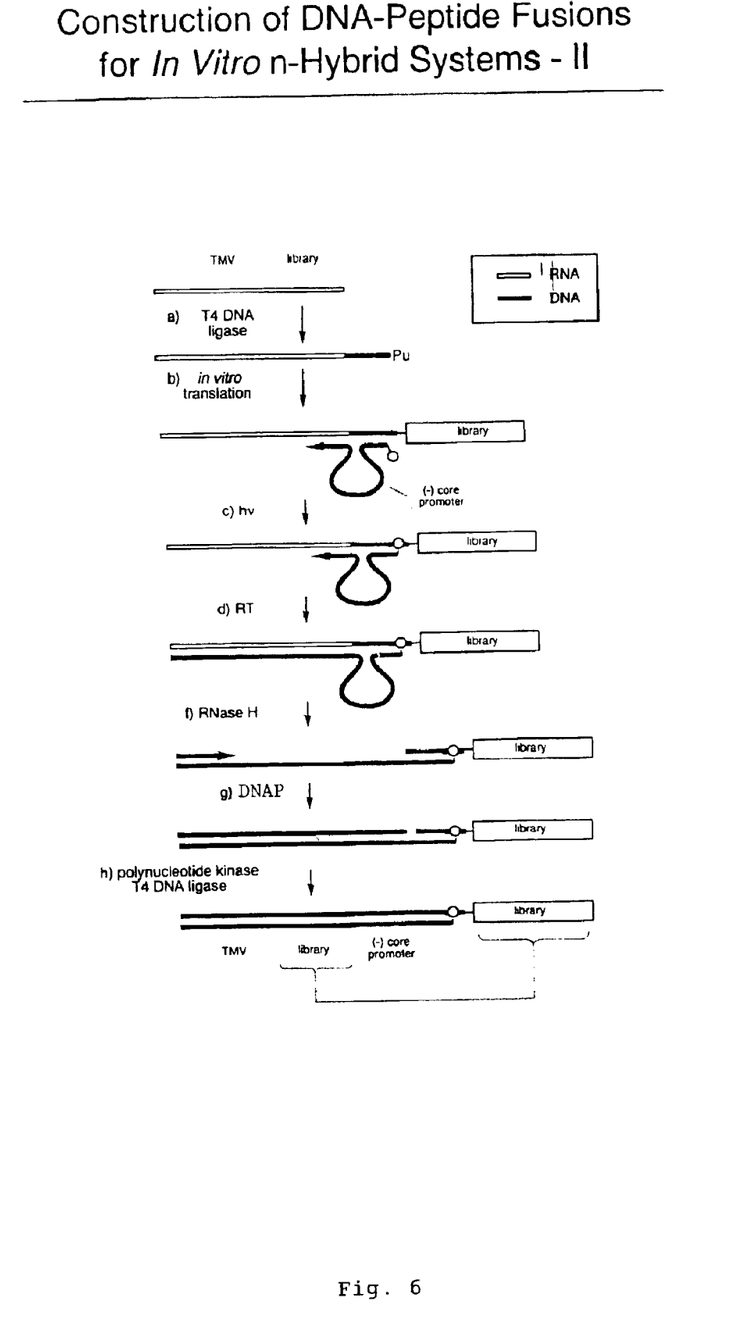
FIG. 6 is a schematic drawing illustrating another exemplary method for the construction of DNA-protein fusions. In this method, the core promoter is located entirely on the reverse transcription primer and is not translated.

In a variant of this approach, the (−) core promoter sequence is completely omitted from the mRNA. This allows the formation of an RNA-protein fusion intermediate that is devoid of a potentially unwanted C-terminal amino acid sequence. The promoter is introduced by hybridization of a reverse transcription primer that contains the complete promoter sequence and forms a bulge structure upon binding to the target RNA-protein fusion (see FIG. 6). Synthesis of a dsDNA-protein fusion is then carried out as described above.

Figure 7:
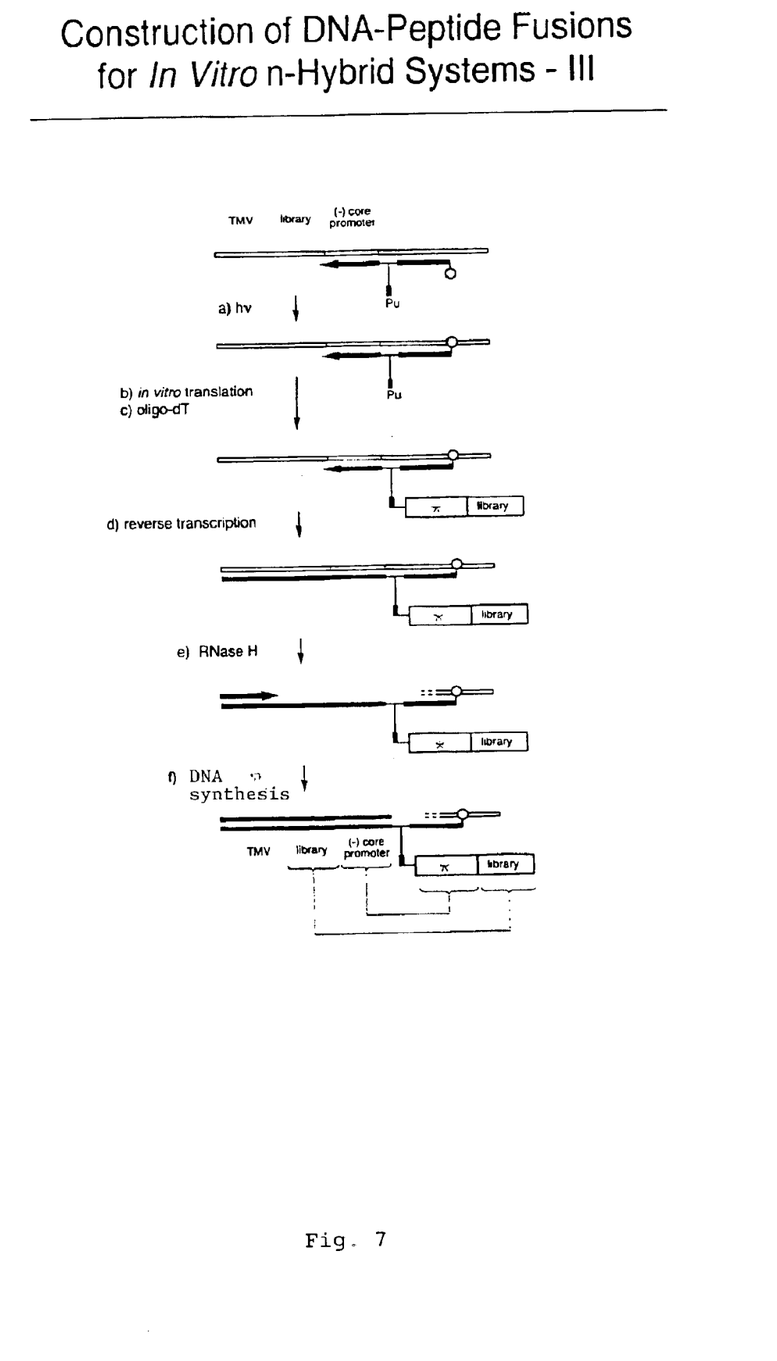
FIG. 7 is a schematic drawing illustrating another exemplary method for the construction of DNA-protein fusions. In this method, a portion of the core promoter is located on the RNA and is translated into the protein C-terminus (indicated by an asterisk).
Figure 8:
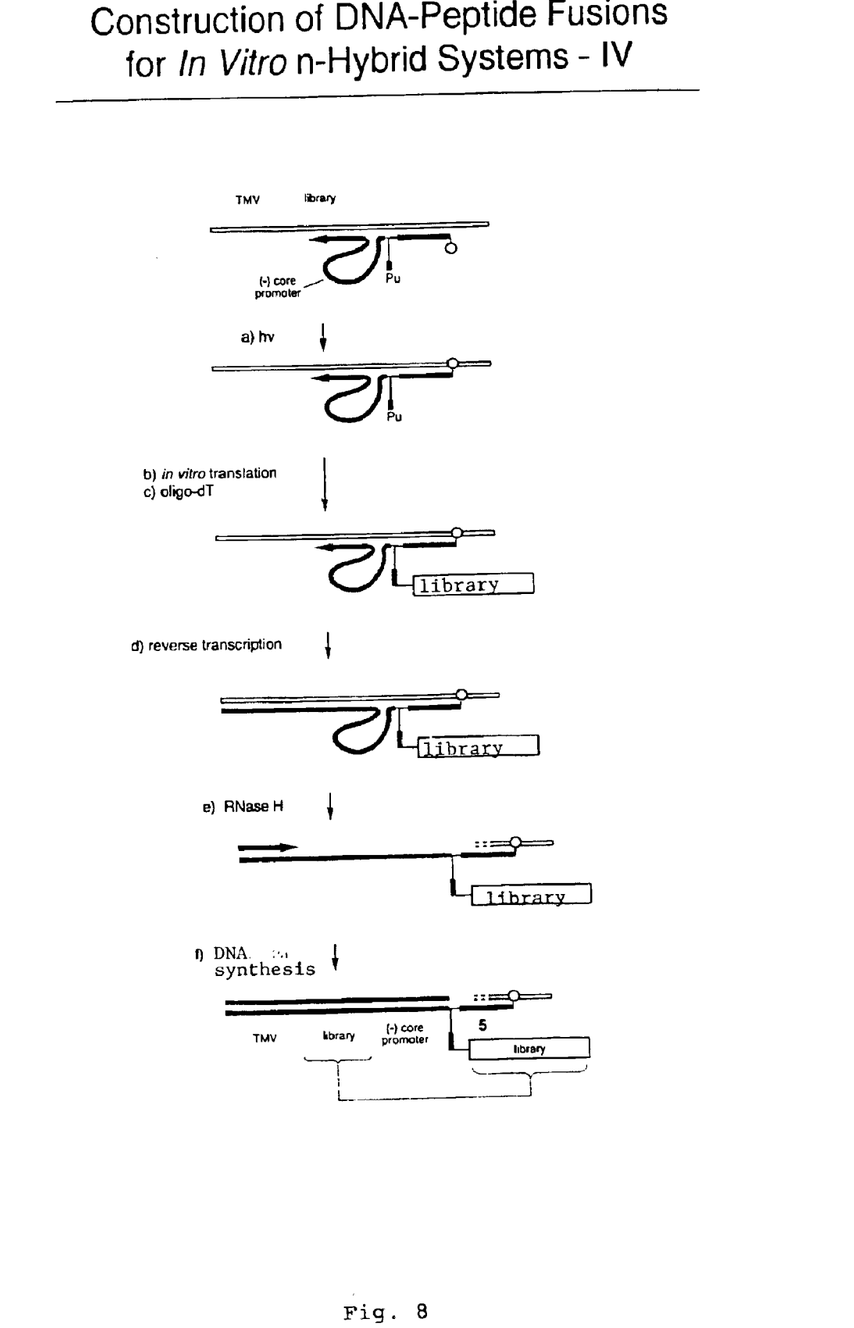
FIG. 8 is a schematic drawing illustrating yet another exemplary method for the construction of DNA-protein fusions. In this method, the core promoter is located entirely on the reverse transcription primer and is not translated.

In yet another approach, the required DNA-protein fusions are constructed by using a combined puromycin-linker/reverse transcription primer construct (FIG. 7; Type B3 in Lohse et al., WO 00/32823). The template RNA includes translation initiation sequences, a coding sequence for the desired protein (or protein library member), and a sequence that corresponds to a core promoter for basal transcription (Corden et al., Science (1980) vol. 209, p. 1406–1414) in reverse orientation, followed by some additional sequences used for specific functions during the synthetic process (see Type B3 in Lohse et al., WO 00/32823). DNA-protein fusion preparation follows a previously described protocol (see Type B3 synthesis in Lohse et al., U.S. Ser. No. 09/453,190; WO 00/32823). Again, due to the nature of the template RNA, a portion of the translated protein corresponds to the promoter sequence. In a variation of this strategy similar to that described above, the promoter may be omitted entirely from the mRNA and included in the linker/primer construct (FIG. 8). Upon binding to the target RNA, the promoter sequence forms a bulge structure. As above, a series of reverse transcription, RNase H, and second strand DNA synthesis treatments generate the desired dsDNA-protein fusions useful for the in vitro two-hybrid and three-hybrid experiments described herein.

For all of the constructs described above, the precise promoter, its relative location with respect to the gene and protein portion, the nature of the puromycin-linker, the inclusion of additional amino acid sequences that modulate the spatial arrangement of the protein, and the like may be optimized by standard experimental techniques.

Construction of Target Compound Fusion Molecules

If the desired target ("B" in FIGS. 1–4) is a protein or peptide, it is preferably cloned and expressed as a fusion protein with an appropriate transcription activation domain, for example, herpesvirus VP16 (Chasman et al., Mol. Cell. Biol. (1989) vol. 9, p. 4746–4749). Alternatively, the desired activation domain can be synthesized separately (either by recombinant techniques or chemical synthesis) and chemically coupled to a target molecule, for example, a small molecule drug (Nyanguile et al., Proc. Natl. Acad. Sci. USA (1997) vol. 94, p. 13402–13406). Chemical coupling may also be utilized for protein and nucleic acid targets.

In general, in choosing transcription activation domains and constructing target compound fusion molecules, considerations similar to those previously described for classical yeast two- and three-hybrid systems apply (for reviews, see, e.g., Kolanus, Curr Top Microbiol Immunol. (1999) vol. 243, p. 37–54; Vidal & Legrain, Nucleic Acids Res. (1999), vol. 27, p. 4; and Drees, Curr. Opinion Chem. Biol. (1999) vol. 3, p. 64–70). If desired, the potency of an activation domain may be enhanced by attachment of multiple copies of the domain to the target molecule (Natesan et al., Proc. Natl. Acad. Sci. (1999) vol. 96, p. 13898–13903).

In Vitro Two-Hybrid Systems

To measure transcription of activated genes according to the present methods, any standard in vitro transcription system may be utilized. Preferably, assays are performed in a manner similar to previously described eukaryotic in vitro systems for the study of transcription activators (e.g., Gaudreau et al., Mol. Cell (1998) vol. 1, p. 913–916; Carey et al., Science (1990) vol. 247, p. 710–712; Chasman et al., Mol. Cell. Biol. (1989) vol. 9, p. 4746–4749; Haile & Parvin, J. Biol. Chem. (1999) vol. 274, p. 2113–2117; and Nyanguile et al. (Proc. Natl. Acad. Sci. USA (1997) vol. 94, p. 13402–13406).

For the construction of an in vitro two-hybrid system, suitable DNA-protein fusions (for example, as constructed by the methods above) are incubated in an appropriate eukaryotic in vitro transcription system (e.g., HeLa nuclear extract; Carey et al., Science (1990) vol. 247, p. 710–712), and the desired target compound fusion molecule is added (FIG. 1B). The association of the target compound "B" with the protein portion "A" of the DNA-protein fusion molecule triggers binding of the RNA polymerase complex to the core promoter sequence and initiation of transcription in cis. Reaction times may be adjusted, depending on the strength of the protein-target A-B interaction; generally, longer incubations lead to higher RNA yields. Even very weak binding affinities may be measured successfully by assaying RNA synthesis over longer periods of time. The presence of the newly synthesized RNA is then detected by any standard method, for example, through detection of incorporated radiolabelled NTPs or by primer extension assays (Carey et al., Science (1990) vol. 247, p. 710–712). When using DNA-protein fusions of known sequence, this method may be used for analysis of molecular interactions between the protein "A" and the target molecule "B."

It is important to note that the transcribed RNA contains the genetic information (in antisense format) for proteins that promote target binding because transcriptional activation is assumed to occur selectively in cis. Thus, recovery of the RNA allows amplification of the protein coding sequence, its identification, and transmission of the genetic information. This is of great importance when the population of DNA-protein fusions is not uniform, but rather represents a diverse mixture or library of different molecules. Under optimized conditions, the background transcription of DNA-protein fusions that do not actively promote recruitment of the RNA polymerase through activator binding is believed to be relatively low. Hence the synthesized RNA becomes selectively enriched in sequences that encode those molecules "A" that possess considerable target binding affinities.

This aspect of the present assays also enables the design of in vitro selection schemes (FIG. 9). As shown in FIG. 9, the RNA product is isolated from a transcription reaction mixture and used as a template for the generation (for example, by a standard RT-PCR reaction) of double-stranded DNA molecules corresponding to the transcribed RNA product(s). To avoid the amplification of unwanted sequences, it is of particular importance to completely remove the DNA (i.e., the fusion molecules), for example, through prior DNase treatment. PCR primers are designed to generate a dsDNA template containing desired 5' and 3' sequences for the concomitant synthesis of an mRNA that is utilized for DNA-protein fusion synthesis (for example, as described above). Preferably, the forward primer is designed to introduce a promoter sequence (for example, a T7 promoter sequence) upstream of the template region; the reverse primer restores the sequence for the desired RNA 3'-end. RNA synthesis with T7 transcriptase completes a cycle of in vitro selection. After a few rounds of selection, those sequences that represent the best binders dominate the population and may be readily isolated as RNA or double-stranded DNA sequences, and subjected to sequence and structure determination.

In Vitro Three-Hybrid Systems

In addition to two-hybrid systems, the use of DNA-protein fusions also facilitates the development of multi-component assays. These are useful, for example, when protein portion "A" does not directly interact with "B," but rather requires an additional adaptor or mediator molecule "M" to promote binding (FIG. 2B). This assay may be used in any context recommended for traditional three-hybrid systems (for reviews, see Kolanus, Curr Top Microbiol Immunol. (1999) vol. 243, p. 37–54; Vidal & Legrain, Nucleic Acids Res. (1999), vol. 27, p. 4; and Drees, Curr. Opinion Chem. Biol. (1999) vol. 3, p. 64–70). Assays are carried out as described above for the in vitro two-hybrid system, except that the "M" component is also included in the in vitro transcription reaction mixture. These assays may be carried out to determine whether any particular three components interact, as well as to perform in vitro selection experiments for screening DNA-protein fusion libraries.

In Vitro Reverse Two-Hybrid Systems

Figure 4:
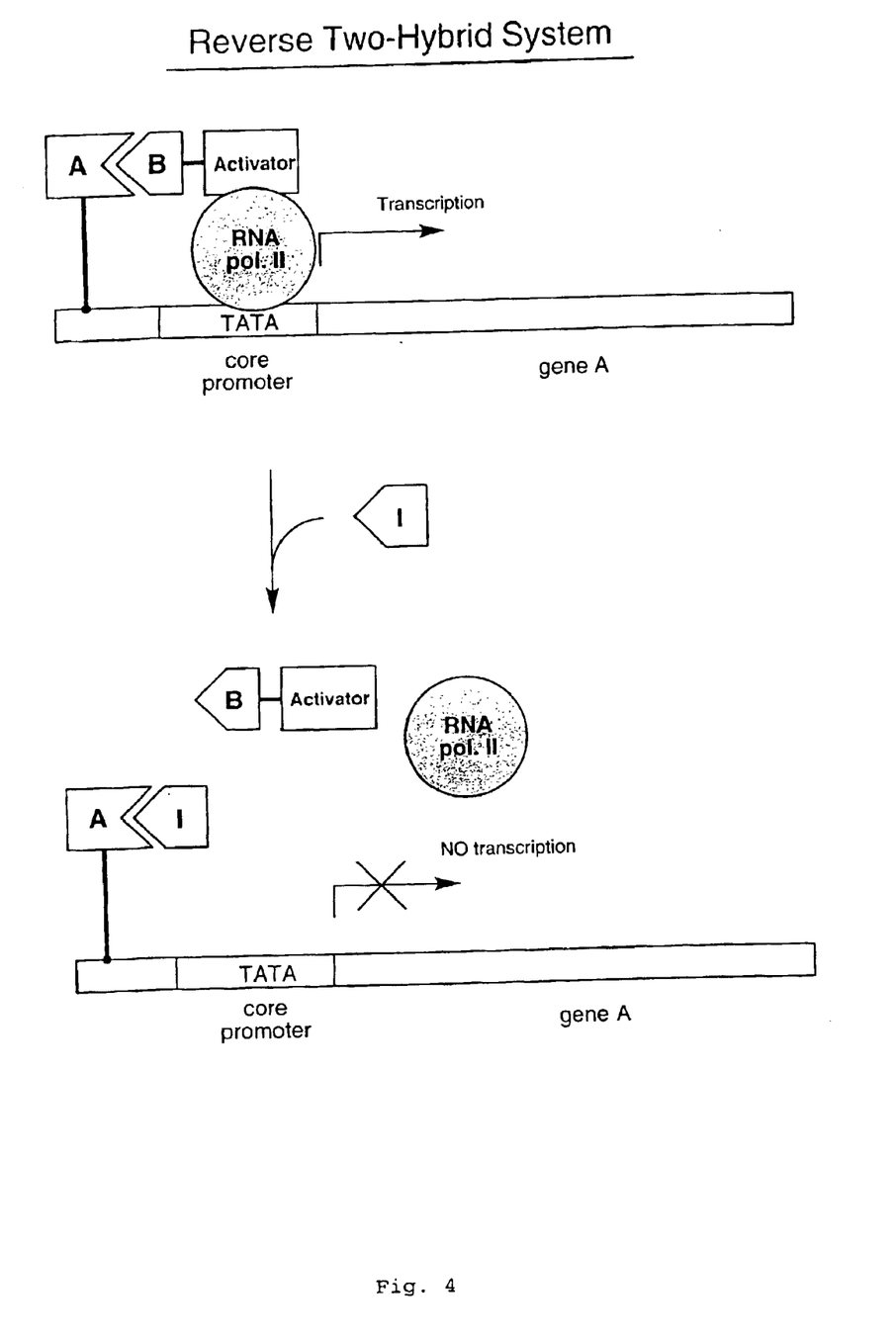
FIG. 4 is a schematic drawing illustrating an in vitro reverse two-hybrid system using DNA-protein fusions. The presence of inhibitor "I" abolishes the interaction between "A" and "B" and thus represses transcription.

Reverse two-hybrid systems can also be carried out using the components described herein. In this assay, an inhibitor "I" reduces or abolishes the transcription output by interference with binding or competitive binding to the target compound or protein domain "A" (FIG. 4). Reverse two-hybrid assays are most useful for screening proteins, peptides, and small molecule drugs for those that interact with known proteins, such as receptors. In addition, these assays may be conducted as described above to detect an inhibitor of a multimeric target complex (e.g., "M-B" in FIG. 2B) or transcriptional activator protein (FIG. 3).

In Vitro Assays for Transcriptional Activator Proteins

Another assay system enabled by the in vitro DNA-protein fusion format described herein is a one-hybrid system that can be utilized to identify or select for transcriptional activator proteins (FIG. 3). As shown in FIG. 3, this format is carried out using individual DNA-protein fusion molecules to identify those having transcriptional activation potential, or in an in vitro selection format to screen DNA-protein fusion libraries for transcriptional activator proteins. In this assay, only the DNA-protein fusion molecule is added to the in vitro transcription reaction mixture, and an increase in RNA product signals transcriptional activation potential.

Other Embodiments

Although the present invention has been described with reference to preferred embodiments, one skilled in the art can easily ascertain its essential characteristics and without departing from the spirit and scope thereof, can make various changes and modifications of the invention to adapt it to various usages and conditions. Those skilled in the art will recognize or be able to ascertain using no more than routine experimentation, many equivalents to the specific embodiments of the invention described herein. Such equivalents are intended to be encompassed in the scope of the present invention.

All publications, patents, and patent applications mentioned in this specification are herein incorporated by reference.

What is claimed is:

1. A method for determining whether a protein interacts with a target compound in vitro, said method comprising the steps of:
   (a) providing a DNA-protein fusion molecule comprising (i) a double-stranded DNA having a core promoter operably linked to a nucleic acid sequence, and (ii) a protein covalently attached to said DNA;
   (b) providing a target compound fusion molecule comprising a target compound covalently attached to a transcription activation domain;
   (c) contacting said DNA-protein fusion molecule with said target compound fusion molecule in an in vitro transcription system under conditions that allow said target compound fusion molecule to interact with the protein of said DNA-protein fusion molecule, wherein an interaction recruits RLNA polymerase and triggers transcription of said nucleic acid sequence; and
   (d) detecting increased transcription of said nucleic acid sequence, or a portion thereof, in the presence of said target compound fusion molecule as an indication that the protein of said DNA-protein fusion interacts with the target compound of said target compound fusion molecule.

2. A method for determining whether a protein interacts in vitro with a target compound through an adaptor molecule, said method comprising the steps of:
   (a) providing a DNA-protein fusion molecule comprising (i) a double-stranded DNA having a core promoter operably linked to a nucleic acid sequence, and (ii) a protein covalently attached to said DNA;
   (b) providing a target compound fusion molecule comprising a target compound covalently attached to a transcription activation domain;
   (c) contacting said DNA-protein fusion molecule with said target compound fusion molecule in the presence of an adaptor molecule, wherein said adaptor molecule is necessary for an interaction to occur between the protein of said DNA-protein fusion molecule and said target compound fusion molecule, said contacting being carried out in an in vitro transcription system under conditions that allow said DNA-protein fusion molecule, said adaptor molecule, and said target compound fusion molecule to interact, wherein an interaction recruits RNA polymerase and triggers transcription of said nucleic acid sequence; and
   (d) detecting increased transcription of said nucleic acid sequence, or a portion thereof, in the presence of said target compound fusion molecule as an indication that the protein of said DNA-protein fusion interacts with the target compound of said target compound fusion molecule in the presence of said adaptor molecule.

3. The method of any one of claims 1–2, wherein said target compound is selected from the group consisting of a protein, a nucleic acid, or a small molecule.

4. The method of any one of claims 1–2, wherein said transcription activation domain is the herpesvirus VP16 polypeptide.

5. The method of any one of claims 1–2, wherein said DNA-protein fusion is characterized by said protein being covalently attached to said DNA 5' to said core promoter.

6. The method of claim 1, wherein the nucleic acid sequence comprises an open reading frame encoding said protein.

7. The method of claim 2, wherein the nucleic acid sequence comprises an open reading frame encoding said protein.

* * * * *

UNITED STATES PATENT AND TRADEMARK OFFICE
CERTIFICATE OF CORRECTION

PATENT NO. : 6,951,725 B2
DATED : October 4, 2005
INVENTOR(S) : Kurz et al.

It is certified that error appears in the above-identified patent and that said Letters Patent is hereby corrected as shown below:

Column 13,
Line 33, "RLNA" should read -- RNA. --.

Signed and Sealed this

Thirtieth Day of May, 2006

JON W. DUDAS
*Director of the United States Patent and Trademark Office*